(12) United States Patent
McKinley et al.

(10) Patent No.: US 9,475,526 B2
(45) Date of Patent: Oct. 25, 2016

(54) TRACK LINK HAVING A WEAR SENSING DEVICE

(71) Applicant: Caterpillar Inc., Peoria, IL (US)

(72) Inventors: Timothy Allen McKinley, Peoria, IL (US); Andrew Alfred Knitt, Oconomowoc, WI (US); Mark Steven Diekevers, Germantown Hills, IL (US)

(73) Assignee: Caterpillar Inc., Peoria, IL (US)

( * ) Notice: Subject to any disclaimer, the term of this patent is extended or adjusted under 35 U.S.C. 154(b) by 36 days.

(21) Appl. No.: 14/466,982

(22) Filed: Aug. 23, 2014

(65) Prior Publication Data

US 2016/0052572 A1    Feb. 25, 2016

(51) Int. Cl.
| | |
|---|---|
| *B62D 55/20* | (2006.01) |
| *B62D 55/21* | (2006.01) |
| *B62D 55/32* | (2006.01) |
| *G01N 3/06* | (2006.01) |
| *G01B 21/18* | (2006.01) |

(52) U.S. Cl.
CPC ............ *B62D 55/21* (2013.01); *B62D 55/202* (2013.01); *B62D 55/32* (2013.01); *G01B 21/18* (2013.01); *G01N 3/06* (2013.01)

(58) Field of Classification Search
CPC ..... B62D 55/20; B62D 55/202; B62D 55/21
See application file for complete search history.

(56) References Cited

U.S. PATENT DOCUMENTS

| | | |
|---|---|---|
| 3,815,426 A | 6/1974 | Rohner |
| 3,958,445 A | 5/1976 | Howard et al. |
| 4,423,910 A * | 1/1984 | Narang .................. B62D 55/20 305/100 |
| 4,646,001 A * | 2/1987 | Baldwin ................ B04C 11/00 188/1.11 L |
| 4,790,190 A | 12/1988 | Bambara et al. |
| 4,928,521 A | 5/1990 | Jardine |
| 5,348,515 A | 9/1994 | Miller |
| 5,436,612 A | 7/1995 | Aduddell |
| 5,636,026 A | 6/1997 | Mian et al. |
| 5,749,635 A | 5/1998 | Umbarger |
| 6,024,183 A | 2/2000 | Dietz et al. |
| 6,027,185 A | 2/2000 | Crabb |

(Continued)

FOREIGN PATENT DOCUMENTS

| | | |
|---|---|---|
| CN | 203651952 | 6/2014 |
| EP | 2 175 423 | 4/2010 |

(Continued)

OTHER PUBLICATIONS

Zhange, Z X et al., Measurements of cutter forces and cutter temperature of boring machine in Aspo Hard Rock Laboratory, Tech. Rpt TR-01-34, Apr. 2001.

(Continued)

*Primary Examiner* — John Walters
*Assistant Examiner* — James Triggs
(74) *Attorney, Agent, or Firm* — Finnegan, Henderson, Farabow, Garrett & Dunner, LLP (57) ABSTRACT

A track link having a wear sensing device is disclosed. The track link may include a link body including a surface, a cavity, and at least one hole configured to receive a track pin. The track link may further include the wear sensing device positioned in the cavity. The wear sensing device may be configured to generate a signal indicative of a wear parameter of the surface. The track link may further include a containment mechanism configured to secure the wear sensing device in position inside the cavity.

15 Claims, 5 Drawing Sheets

(56) References Cited

U.S. PATENT DOCUMENTS

| | | | |
|---|---|---|---|
| 6,107,917 | A | 8/2000 | Carrender et al. |
| 6,250,429 | B1 | 6/2001 | Kramer |
| 6,276,768 | B1 | 8/2001 | Miller |
| 6,305,763 | B1 | 10/2001 | Oertley |
| 6,354,678 | B1 | 3/2002 | Oertley |
| 6,360,850 | B1 | 3/2002 | Odisho et al. |
| 6,431,008 | B1 | 8/2002 | Oertley et al. |
| 6,477,893 | B1 | 11/2002 | Djordjevic |
| 6,569,046 | B1 | 5/2003 | Gregg |
| 6,682,155 | B2 | 1/2004 | Hoff et al. |
| 6,845,306 | B2 | 1/2005 | Henry et al. |
| 6,868,711 | B2 | 3/2005 | Ebi |
| 6,948,783 | B2 | 9/2005 | Hoff |
| 7,014,271 | B2 | 3/2006 | Burger et al. |
| 7,032,740 | B2 | 4/2006 | Hochhaus et al. |
| 7,172,257 | B2 | 2/2007 | Tamaru et al. |
| 7,177,553 | B2 | 2/2007 | Ono |
| 7,210,750 | B2 | 5/2007 | Yamamoto et al. |
| 7,237,631 | B2 | 7/2007 | Livesay et al. |
| 7,239,242 | B2 | 7/2007 | Park et al. |
| 7,374,257 | B2 | 5/2008 | Oertley |
| 7,507,965 | B2 | 3/2009 | Lane et al. |
| 7,540,374 | B2 | 6/2009 | Rathbun et al. |
| 7,698,946 | B2 | 4/2010 | Clarke et al. |
| 7,764,173 | B2 | 7/2010 | Yamagiwa |
| 7,908,928 | B2 | 3/2011 | Vik et al. |
| 7,914,086 | B2 | 3/2011 | Mulligan |
| 8,100,483 | B2 | 1/2012 | Diekevers et al. |
| 8,169,311 | B1 | 5/2012 | Breed |
| 8,326,549 | B2 | 12/2012 | Ishizaki et al. |
| 8,335,606 | B2 | 12/2012 | Mian et al. |
| 8,398,182 | B2 | 3/2013 | Simula et al. |
| 8,426,813 | B2 | 4/2013 | Furry |
| 8,540,325 | B2 | 9/2013 | Diekevers et al. |
| 8,543,283 | B2 | 9/2013 | Boss et al. |
| 8,596,126 | B2 | 12/2013 | Oliver et al. |
| 8,600,611 | B2 | 12/2013 | Seize |
| 2002/0116992 | A1 | 8/2002 | Rickel |
| 2006/0044146 | A1 | 3/2006 | Ferguson et al. |
| 2006/0243839 | A9 | 11/2006 | Barsevicius et al. |
| 2007/0044447 | A1 | 3/2007 | Viaud |
| 2007/0088523 | A1 | 4/2007 | Keller et al. |
| 2009/0099886 | A1 | 4/2009 | Greiner et al. |
| 2009/0297273 | A1 | 12/2009 | Lindbergh et al. |
| 2009/0313860 | A1 | 12/2009 | Breiner et al. |
| 2010/0013594 | A1 | 1/2010 | Komine et al. |
| 2011/0046857 | A1 | 2/2011 | Farmer et al. |
| 2012/0043980 | A1 | 2/2012 | Davies |
| 2013/0082846 | A1 | 4/2013 | McKinley et al. |
| 2013/0255354 | A1 | 10/2013 | Hawkins et al. |
| 2014/0083782 | A1 | 3/2014 | Brewer et al. |
| 2014/0105481 | A1 | 4/2014 | Hasselbusch et al. |
| 2014/0229120 | A1 | 8/2014 | Luharuka et al. |

FOREIGN PATENT DOCUMENTS

| | | |
|---|---|---|
| EP | 2 548 665 | 1/2013 |
| GB | 1515450 | 6/1978 |
| JP | 2000-042894 | 2/2000 |
| KR | 101067961 | 5/2011 |
| WO | WO 99/51996 | 10/1999 |
| WO | WO 2006/116758 | 11/2006 |
| WO | WO 2010/117331 | 10/2010 |
| WO | WO 2013/057275 | 4/2013 |
| WO | WO 2014/00507 | 1/2014 |

OTHER PUBLICATIONS

De Broissia, M. et al, "Global Optimisation of Disc Cutter Tool Life for Tunnel Boring Machine Preparing 4th Eurothen Workshop" *Bougues Travaux Publics*.

EPO International Search Report, PCT/US2006/016518, filing date Oct. 30, 2006.

EPO International Search Report, PCT/US2012/057831, filing date Sep. 28, 2012.

Shanahan, A. Cutter Instrumentation System for Tunnel boring Machines, *The Robbins Co.*, Kent, WA available Sep. 17, 2010.

Hasselbusch, Michael, et al., "Track Assembly Having a Wear Monitoring System," U.S. Appl. No. 14/534,649, filed Nov. 6, 2014.

Rust, Craig, "Thrust Bias Detection System," U.S. Appl. No. 14/537,204, filed Nov. 10, 2014.

Behmlander, Matthew J., et al., "Erosion Monitoring System For Ground Engaging Tool," U.S. Appl. No. 13/866,394, filed Apr. 19, 2013.

McKinley, Timothy Allen, et al., "Sensor System and Method," U.S. Appl. No. 13/628,662, filed Sep. 27, 2012.

\* cited by examiner

TRACK LINK HAVING A WEAR SENSING DEVICE

TECHNICAL FIELD

The present disclosure is directed to a track link and, more particularly, to a track link having a wear sensing device.

BACKGROUND

A mobile machine may be used to perform various types of work on different worksites, such as a construction site, a demolition site, a mining site, or a landfill site. For example, a bulldozer may be used to push soil and rock on a construction site. The bulldozer, as a track-type mobile machine, includes a tracked undercarriage with tracks on the left and right sides of the machine. Each of the tracks includes a chain formed by connecting a number of track links to one another, and connecting a number of track shoes to the chains. The tracks are supported by various roller assemblies on both sides of the machine.

Operation of the mobile machine inevitably results in wear or damage to various components, including components of the undercarriage such as the track links and the roller assemblies. For example, as a track assembly operates, a surface of each track link may wear away through contact with other components of the track assembly, machine, and/or outside materials (e.g., the ground). It is known to service or replace a machine component, for example, when the component exceeds its expected lifetime (based on the age of the component or number of hours of use experienced by the component), or based on the results of inspection or evaluation of the component.

These known methods for determining when components are to be serviced or replaced suffer from numerous disadvantages. For example, a particular machine component may be capable of being used far in excess of its expected lifetime, and thus replacement of the component based solely on age may be premature and result in unnecessary costs and machine down-time. Conversely, a particular machine component may fail well in advance of its expected lifetime, and continued operation of the machine with the damaged component may result in damage to other components of the machine. Similarly, inspection and evaluation of a machine component may result in unnecessary costs and machine down-time when it is determined that service or replacement of the component is not required. Still further, inspection and evaluation may require that the machine be evaluated by temporarily installing various sensors throughout the machine, with extensive cabling connecting the sensor to a computer that collects data and other information from the sensors. The cabling prevents the machine from being operated on the worksite, and thus such evaluation does not provide information relating to the actual use of the machine while performing work.

Thus, there exists a need for an improved monitoring system for collecting information, such as wear information, related to a mobile machine. The present disclosure is directed to overcoming one or more of the problems set forth above and/or other problems of the prior art.

SUMMARY

In one aspect, a track link for a track assembly of a machine is disclosed. The track link may include a link body including a surface, a cavity, and at least one hole configured to receive a track pin. The track link may further include a sensing device positioned in the cavity and configured to generate a signal indicative of a wear parameter of the surface. The track link may further include a containment mechanism configured to secure the sensing device in position inside the cavity.

In another aspect, a method of installing a sensing device in a track link is disclosed. The method may include forming a cavity in a link body of the track link, the cavity adjacent to a first surface. The method may also include positioning the sensing device inside the cavity. The method may further include holding the sensing device in position within the cavity with a containment mechanism. The sensing device may be positioned inside the cavity such that the sensing device is configured to detect a wear parameter of the first surface.

In yet another aspect, a detection system for a track assembly of a machine is disclosed. The detection system may include a track link including a surface, and a sensing device secured to the track link and configured to detect a wear parameter of the surface. The detection system may further include a communication device mounted to the machine and configured to communicate with the sensing device. The sensing device may be configured to generate a signal indicative of the wear parameter and transmit the signal to the communication device, and the communication device may be configured to transmit a corresponding signal indicative of the wear parameter to a computing device.

DETAILED DESCRIPTION

Figure 1:
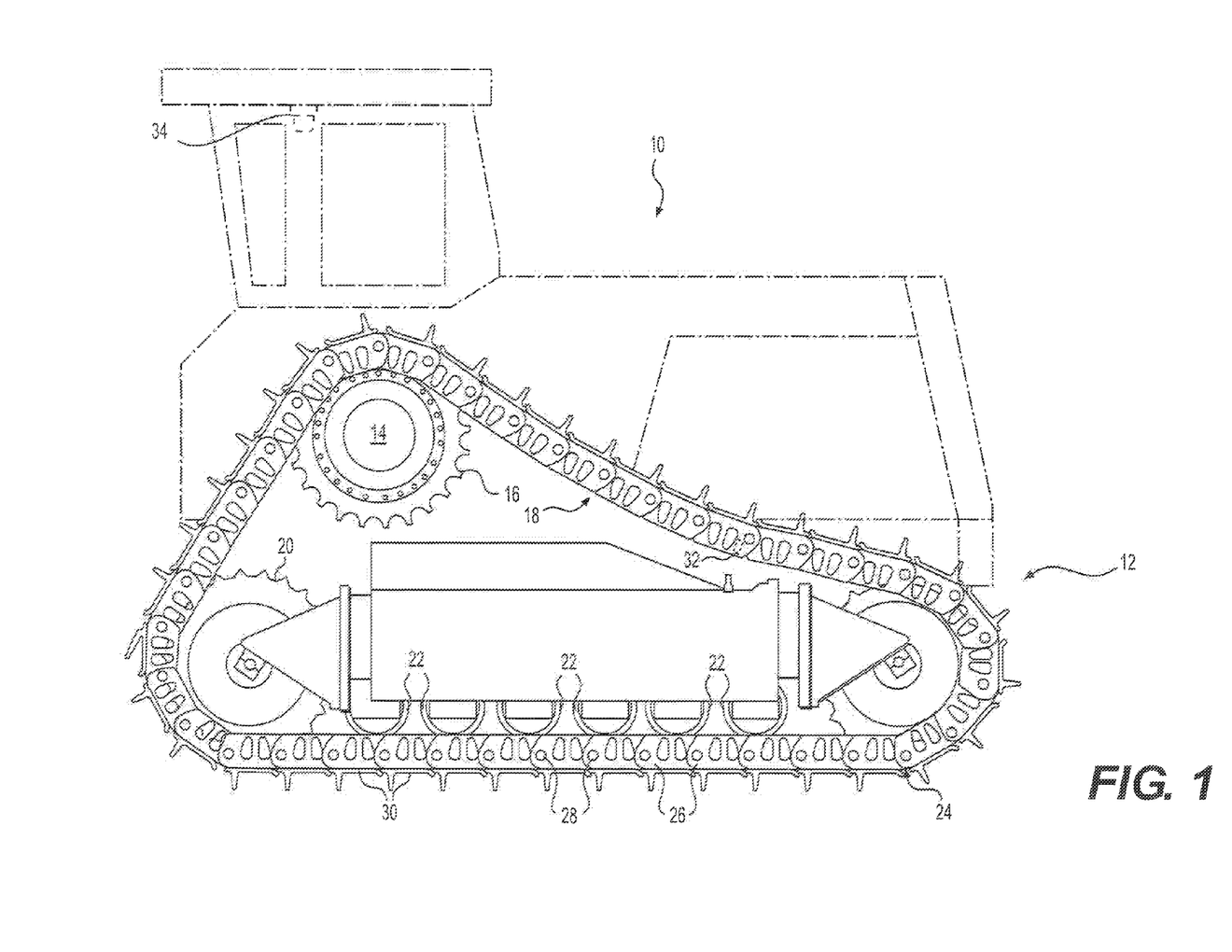
FIG. 1 illustrates an exemplary track-type machine, consistent with disclosed embodiments.

FIG. 1 illustrates an exemplary track-type machine 10, consistent with disclosed embodiments. Track-type machine 10 may embody any machine that is driven, propelled, positioned, and/or maneuvered by operating a "continuous" track-type traction device. Such machines may include, for example, track-type tractors, skid steers, dozers, excavators, backhoes, track loaders, front shovels, rope shovels, or any other type of track-maneuverable machine. Machine 10 may include a pair of track assemblies 12 (only one shown) on opposing sides of machine 10 and driven by a driving mechanism 14. Track assembly 12 may include a drive sprocket 16 coupled to driving mechanism 14, and a chain assembly 18 operatively coupled to driving mechanism 14 by drive sprocket 16 and configured to propel machine 10 when driven by driving mechanism 14.

Driving mechanism 14 may include one or more components configured to generate a torque output. For example, driving mechanism 14 may include any suitable type of internal combustion engine, such as a gasoline, diesel, natural gas, or hybrid-powered engine or turbine. Alternatively or additionally, driving mechanism 14 may embody an electric motor, electrically coupled to an electric power source and configured to convert at least a portion of the electrical energy from the electric power output into mechanical energy. According to yet another embodiment, driving mechanism 14 may include a hydraulic motor fluidly coupled to a hydraulic pump and configured to convert a fluid pressurized by the pump into a torque output.

Drive sprocket 16 may be coupled to driving mechanism 14 via a shaft (not shown), which may provide an interface for delivering torque generated by driving mechanism 14 to drive sprocket 16. For example, drive sprocket 16 may be secured (e.g., welded, bolted, heat-coupled, etc.) to a hub associated with a shaft (not shown), so that drive sprocket 16 rotates in response to the torque generated by driving mechanism 14. In some embodiments, drive sprocket 16 may be directly coupled via a drive shaft to driving mechanism 14. Alternatively, drive sprocket 16 may be coupled to driving mechanism 14 via a torque converter (such as a gearbox, transmission, etc.), so that rotation of drive sprocket 16 is proportional to the torque generated by driving mechanism 14.

Track assembly 12 may include a plurality of components that form the "continuous" track, ground-engaging portion of the drive system of machine 10. Track assembly 12 may include, among other things, drive sprocket 16, chain assembly 18, at least one idler 20, a plurality of rollers 22, and a traction assembly 24. However, it should be understood that these components of track assembly 12 are exemplary only and not intended to be limiting. Accordingly, track assembly 12 may include additional and/or different components than those listed above.

Chain assembly 18 may form a continuous chain connected around outer portions of drive sprocket 16, idlers 20, and rollers 22. Traction assembly 24 may be connected to an outer portion of chain assembly 18 and configured to engage a ground surface beneath track-type machine 10. In use, rotation of drive sprocket 16 may cause chain assembly 18 to move around drive sprocket 16, idlers 20, rollers 22 and traction assembly 24 to engage the ground and thereby propel track-type machine 10 in a manner known in the art.

In an exemplary embodiment, chain assembly 18 may include a plurality of interconnected track links 26. It should be understood that "track link," as used herein, refers to any linkage component of a continuous chain for a track-type machine, and is not limited to track links 26 described herein. In one embodiment, adjacent (e.g., consecutive) track links 26 may be coupled together via a plurality of track pin assemblies 28. Each track pin assembly 28 may be engaged by teeth of drive sprocket 16 to drive chain assembly 18 around drive sprocket 16, idlers 20, and rollers 22.

Traction assembly 24 may include a plurality of track shoes 30 secured to chain assembly 18. Each track shoe 30 may include a connecting portion configured to be secured to one or more track links 26 and a ground engaging portion configured to contact the ground. The ground engaging portion may include one or more features (e.g., grouser bars) that provide increased traction between track shoes 30 and the ground. It should be understood, however, that the disclosed embodiments may be used with any type of track shoe forming a part of a track assembly used by a track-type mobile machine. In some embodiments, track shoes 30 may be integrally formed with track links 26. In other embodiments, track shoes 30 may be omitted entirely from track assembly 12, so that surfaces of track links 26 that would otherwise contact track shoes 30 may contact the ground surface under machine 10.

In an exemplary embodiment, track-type machine 10 may include one or more components of a detection system configured to monitor a parameter of track assembly 12. For example, track-type machine 10 may include at least one sensing device 32 and at least one communication device 34. Sensing device 32 may be an electronic device configured to detect a parameter of track assembly 12 and transmit a signal indicative of the parameter to communication device 34. Communication device 34 may be configured to forward information received from sensing device 32 to another device, such as an on-board or off-board computer. In this way, information associated with a parameter of track assembly 12 may be automatically determined and routed to an appropriate destination (e.g., for display to an operator).

In an exemplary embodiment, the detection system may be configured to monitor a wear parameter. For example, sensing device 32 may be configured to measure a parameter associated with an amount of wear experienced by a component of track assembly 12 and transmit a signal indicative of the amount of wear to communication device 34. As used herein, a "wear parameter" is a measurement or other characteristic of a monitored component or sensing device 32 that may indicate an amount of wear experienced by the monitored component (when compared to a previous measurement or other previous characteristic, for example).

In an exemplary embodiment, sensing device 32 may be mounted in, on, or around a track link 26 and configured to detect a wear parameter thereof. For example, sensing device 32 may be configured to detect a wear parameter associated with wear of at least one surface of a body of track link 26. In an exemplary embodiment, sensing device 32 may be secured to track link 26. In one embodiment, sensing device 32 may be at least partially embedded in the body of track link 26. In another embodiment, sensing device 32 may be externally mounted to the body of track link 26.

Communication device 34 may be positioned anywhere on machine 10 that allows communication device 34 to receive signals from sensing device 32. As shown in FIG. 1, communication device 34 may be installed in an interior of an operator cabin of machine 10, such as on a ceiling or floor thereof. In other embodiments, communication device 34 may be mounted to an exterior portion of machine 10, such as on top of the operator cabin or on a machine chassis.

Figure 2:
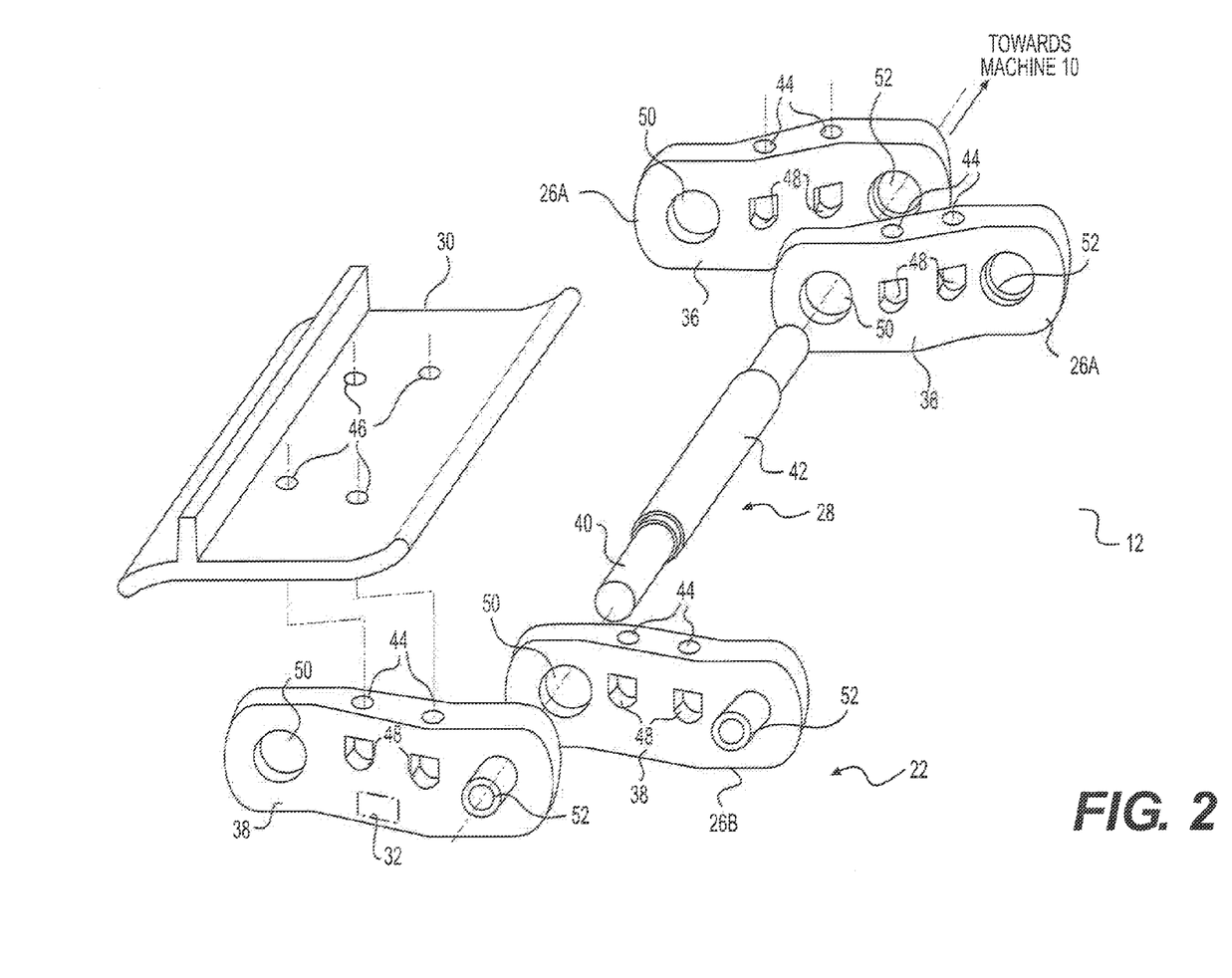
FIG. 2 illustrates an exemplary portion of a track assembly of the track-type machine of FIG. 1.

FIG. 2 illustrates a portion of track assembly 12 in more detail, including four track links 26, one track pin assembly 28, and one track shoe 30. As shown in FIG. 2, track links 26 may include track links 26A and track links 26B. Track links 26A and 26B may be mirror images of each other, and may be disposed opposite one another within track assembly 12, such that track links 26A form one side of track assembly 12 (e.g., side of track assembly nearest to a center of machine 10), while track links 26B form the opposite side of track assembly 12 (e.g., a side of track assembly farthest from the center of machine 10).

When the components shown in FIG. 2 are assembled with one another, one track pin assembly 28 may be used to connect four track links 26 (e.g., two track links 26A and two track links 26B), one track shoe 30 may be connected to one track link 26A and one track link 26B, and another track shoe 30 (not shown) may be connected to the other track link 26A and the other track link 26B.

Each track link 26 may include an inward-facing surface 36 and an outward-facing surface 38. Inward-facing surfaces 36 may face toward a center of chain assembly 18 (e.g., toward the opposite-side chain). Outward-facing surfaces 38 may face away from the center of chain assembly 18 (e.g., toward the center of machine 10 on the side of chain assembly 18 closest to machine 10 and away from the center of machine 10 on the side of chain assembly 18 furthest from machine 10). As shown in FIG. 2, track links 26A, 26B may be connected to each other such that an inward-facing surface 36 is connected to an outward-facing surface 38 of an adjacent track link 26. It should be understood, however, that other track link configurations are possible.

As shown in FIG. 2, each track pin assembly 28 that connects track links 26 may include a track pin 40 and a bushing 42. Bushing 42 may be disposed on track pin 40, such that bushing 42 rotates relative to track pin 40. By this arrangement, drive sprocket 16 (FIG. 1) may engage bushing 42, and bushing 42 may rotate on track pin 40 with drive sprocket 16. As a result of the force applied to bushing 42, track pin 40 may translate, resulting in movement of track assembly 12 to move machine 10 on the ground surface in a manner known in the art.

Each track link 26A and 26B may include one or more through holes 44, while each track shoe 30 may include corresponding through holes 46. Each track link 26A and 26B may also include one or more openings 48 aligned with through hole 44. By this arrangement, threaded fasteners such as bolts (not shown) may be disposed within through holes 44 and 46 to attach track shoes 30 to track links 26A and 26B, and corresponding threaded fasteners such as nuts (not shown) may be disposed on the ends of the bolts. Openings 48 may be formed to facilitate placement or tightening of the nuts on the ends of the bolts, such as by being sized, shaped, or located to accommodate a tool that may be used to tighten the nuts.

Each of track links 26A and 26B may define a plurality of additional through holes 50, 52 configured to receive at least a portion of track pin assemblies 28 in a manner known in the art. For example, through holes 50 may be configured to receive a portion of bushing 42 and through holes 52 may be configured to receive a portion of a free end of track pin 40. In this way, pivot joints may be formed at track pin assemblies 28, allowing chain assembly 18 to move freely around drive sprocket 16, idlers 20, and rollers 22 during operation.

As shown in FIG. 2, one or more of track links 26A, 26B may include sensing device 32. The track link 26A, 26B selected to include sensing device 32 may depend on a number of factors, such as track link position within track assembly 12 and orientation with respect to machine 10, and the means by which sensing device 32 is mounted to the selected track link 26. For example, if either of track links 26A includes sensing device 32, sensing device 32 would be positioned closer to machine 10 than if either of track links 26B includes sensing device 32. Similarly, if sensing device 32 is mounted to or adjacent an inward-facing surface 36 or outward-facing surface 38, the orientation of the selected track link 26 will determine whether sensing device 32 faces toward machine 10 or away from machine 10. In an exemplary embodiment, these factors may be considered when determining the position of a track link 26 that includes sensing device 32.

In one embodiment, a track link 26A, 26B may be selected for including sensing device 32 such that sensing device 32 is capable of reliably communicating with communication device 34. Thus, the track link 26A, 26B that is selected may also depend on a position of communication device 34 on machine 10. As shown in FIG. 2, in an exemplary embodiment sensing device 32 may be mounted to an outward-facing surface 38 of a track link 26B, such that sensing device 32 is positioned farthest from machine 10, and faces away from machine 10. This positioning may allow for reliable communication with communication device 34, since signals may at least partially avoid traveling through components of machine 10 to reach communication device 34. In other embodiments, however, other positions and orientations of sensing device 32 may provide the same or better reliability of communication.

Figure 3:
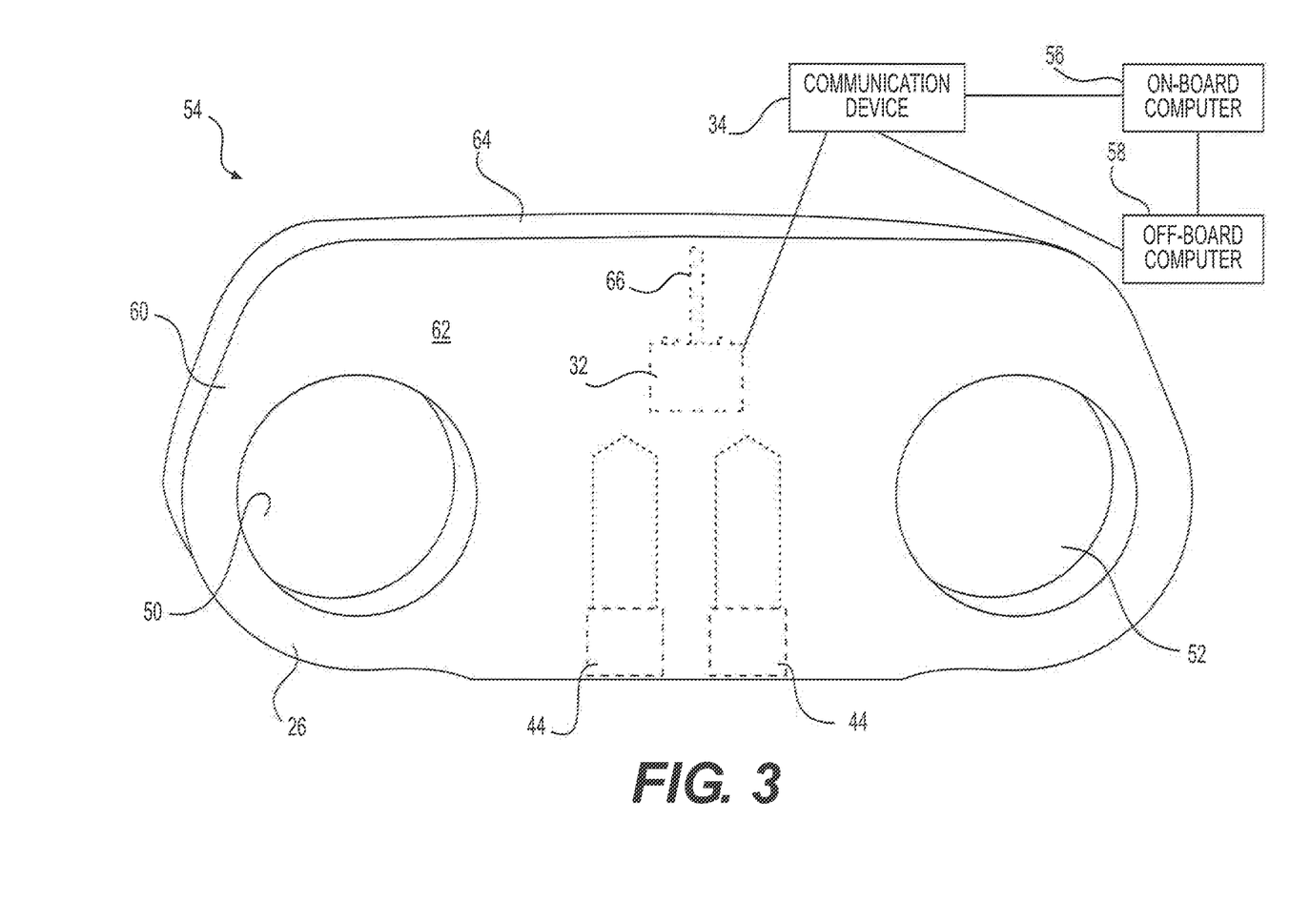
FIG. 3 illustrates an exemplary detection system that may be used in conjunction with the track-type machine of FIG. 1.

FIG. 3 illustrates an exemplary detection system 54 that includes sensing device 32 and communication device 34. In an exemplary embodiment, detection system 54 may also include an on-board computer 56 and an off-board computer 58. Sensing device 32 may be mounted to a track link 26 and configured to transmit a signal indicative of a wear parameter to communication device 34. Communication device 34 may be configured to receive the signal and transmit a corresponding signal to on-board computer 56 and/or off-board computer 58.

As shown in FIG. 3, sensing device 32 may be positioned on or in a link body 60 of a track link 26, proximate to a surface 62 and a surface 64. In one embodiment, sensing device 32 may be positioned within a cavity formed in surface 62 such that sensing device 32 is embedded within link body 60. Sensing device 32 may be secured in a manner that allows signals produced by sensing device 32 to be transmitted outside of link body 60, such as through the cavity, perpendicular to surface 62.

In an exemplary embodiment, sensing device 32 may be positioned adjacent surface 64, which may be a wear surface of link body 60. A wear surface may be any surface of link body 60 in which material wears away during use of track assembly 12. For example, surface 64 may be a wear surface in which material is worn away through contact with other components of track assembly 12 (e.g., rollers 22 or other track guide) and/or external materials (e.g., the ground). Sensing device 32 may be positioned adjacent surface 64 such that sensing device 32 may be configured to detect a wear parameter of surface 64. For example, sensing device 32 may be configured to detect an amount of material that has been worn away from surface 64.

The manner in which sensing device 32 detects a wear parameter may depend on the configuration of sensing device 32. Thus, it should be understood that sensing device 32 is not limited to the configurations described herein, and may include other configurations that allow sensing device 32 to detect a wear parameter of surface 64.

In one embodiment, sensing device 32 may include a wear portion 66 positioned at surface 64 such that, as surface 64 wears away, wear portion 66 also wears away. Sensing device 32 may be configured such that the change in structure of wear portion 66 due to the wear of surface 64 allows sensing device 32 to determine an amount of wear that has occurred (e.g., correlate a dimension, structure, and/or state of wear portion 66 with an amount of material at surface 64 that must have been removed to result in that dimension, structure, and/or state).

In another embodiment, sensing device 32 may detect a wear parameter by measuring a distance from a set point (e.g., an end of sensing device 32) to surface 64. For example, sensing device 32 may use a depth sensor that uses ultrasonic waves, sound waves, lasers, etc. to determine a distance from sensing device 32 to surface 64. As surface 64 wears away, this distance will change, and an amount of material worn away from surface 64 may therefore be determined.

As will be described, sensing device 32 may include one or more components (e.g., antenna, transceiver, transmitter, etc.) that are configured to transmit a signal indicative of a wear parameter of surface 64 to communication device 34. Communication device 34 may be configured to receive the signal and transmit a corresponding signal to on-board computer 56 and/or off-board computer 58. In one embodiment, communication device 34 may include an antenna configured to receive a signal from one device and forward the signal to another device. In some embodiments, communication device 34 may also include a processor and memory for processing and/or storage of information (e.g., wear parameters from sensing device 32).

On-board computer 56 may be a computing device located on machine 10 (e.g., inside the operator cabin). For example, on-board computer 56 may be a dashboard computer including at least a processor and a display. On-board computer 56 may communicate with communication device 34 (e.g., via a wired or wireless connection) to receive wear parameter information. On-board computer 56 may display wear parameter information (e.g., to an operator of machine 10).

Off-board computer 58 may be a similar computing device located away from machine 10 (e.g., inside a control building). Off-board computer 58 may also include at least a processor and a display. Off-board computer 58 may be configured to communicate with communication device 34 and/or on-board computer 56 (e.g., via a wireless network) to similarly receive wear parameter information, which may be displayed to an operator (e.g., a machine supervisor) away from machine 10.

Figure 4:
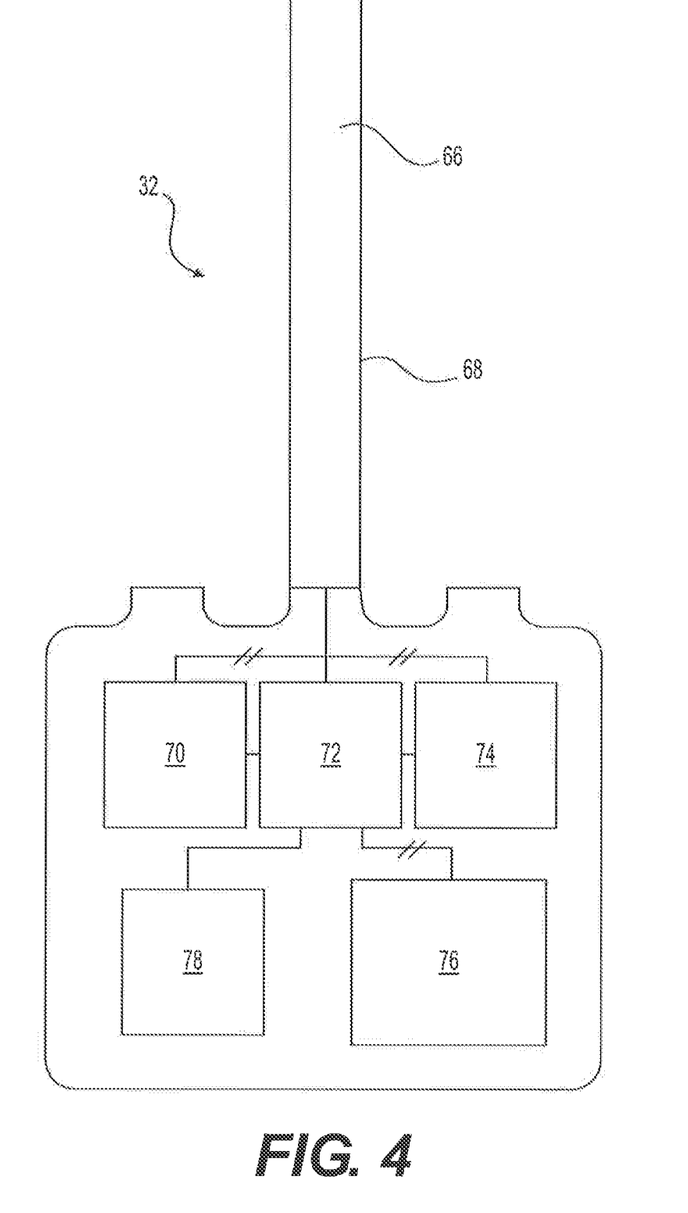
FIG. 4 illustrates an exemplary sensing device that may be used in conjunction with the detection system of FIG. 3.

FIG. 4 illustrates an exemplary embodiment of sensing device 32. Sensing device 32 may include one or more tangible, non-transitory hardware components, including one or more central processing units (CPUs) or processors. For example, sensing device 32 may include a sensing component 68 configured to directly and/or indirectly measure, sense, and/or otherwise receive information (e.g., a wear parameter) as input. In the embodiment of FIG. 4, sensing component 68 may be wear portion 66, which may be a portion of sensing device 32 that is configured to wear away with a wear surface of a track link 26. For example, wear portion 66 may be a resistance member (e.g., one or more resistors) configured such that, as wear portion 66 wears away, a resistance value associated with the resistance member changes. This change in resistance may be correlated with an amount of material at surface 64 that has worn away. In other embodiments, wear portion 66 may take another configuration (e.g., other than being a resistance member, an alternative shape, etc.). Further, in some embodiments, sensing component 68 may not be a wear portion, and may be another device configured to detect a wear parameter (e.g., a depth sensor).

Sensing device 32 may further include circuitry components 70 configured to generate, receive, transmit, and/or modify a signal indicative of a wear parameter detected by sensing device 32. For example, circuitry components 70 may include a signal conditioner, an amplifier, a multiplexer, and/or a converter (e.g., an analog-to-digital (A/D) converter or a digital-to-analog (D/A) converter). It should be understood that these components are exemplary and that additional and/or alternative circuitry components may be used, depending on the configuration of sensing component 68.

A controller 72, such as a low-power microcontroller, may provide an output in response to the input received from sensing component 68 and/or one or more signals processed by any or all of circuitry components 70. A memory device 74, such as either or both of a random-access memory (RAM) and a read-only memory (ROM), may store information related to one or more of the input received from sensing component 68, one or more processed signals from circuitry components 70, and the output from controller 72. Alternatively or additionally, memory device 74 may store instructions used by one or more other components of sensing device 32 (or other component of detection system 54), such as controller 72.

A transceiver 76, such as for example a radio-frequency (RF) transceiver, may wirelessly broadcast the output provided by controller 72 (e.g., to communication device 34). Alternatively or additionally, an output port (not shown), such as for example a USB (universal serial bus) port or similar port, may transmit the output provided by controller 72 through a cable or other connection removably connected to the output port.

A power source 78 may power one or more of the components of sensing device 32. In one embodiment, power source 78 may include a battery, such as a coin-cell type battery. In some embodiments, power source 78 may additionally or alternatively include a motion-based energy source, such as a vibration-based energy-harvesting system, to power one or more of the components of sensing device 32, and/or may be used to charge a battery of power source 78. In yet another embodiment, power source 78 may include a battery capable of being wirelessly charged (e.g., near-field charging). In this way, sensing device 32 may be embedded within link body 60 while being capable of receiving electrical power from outside of link body 60, and thus reducing on-board power (e.g., battery) requirements.

Although FIG. 4 shows examples of specific components used by sensing device 32, sensing device 32 is not limited to the particular configuration shown. Rather, consistent with the disclosure, sensing device 32 may include other components, more components, or fewer components than those described above. Further, it is contemplated that one or more of the hardware components listed above may be implemented in part or wholly using software. One or more of such software components may be stored on a tangible, non-transitory computer-readable storage medium that includes computer-executable instructions that, when executed by a processor or other computer hardware, perform methods and processes consistent with the disclosure.

Figure 5:
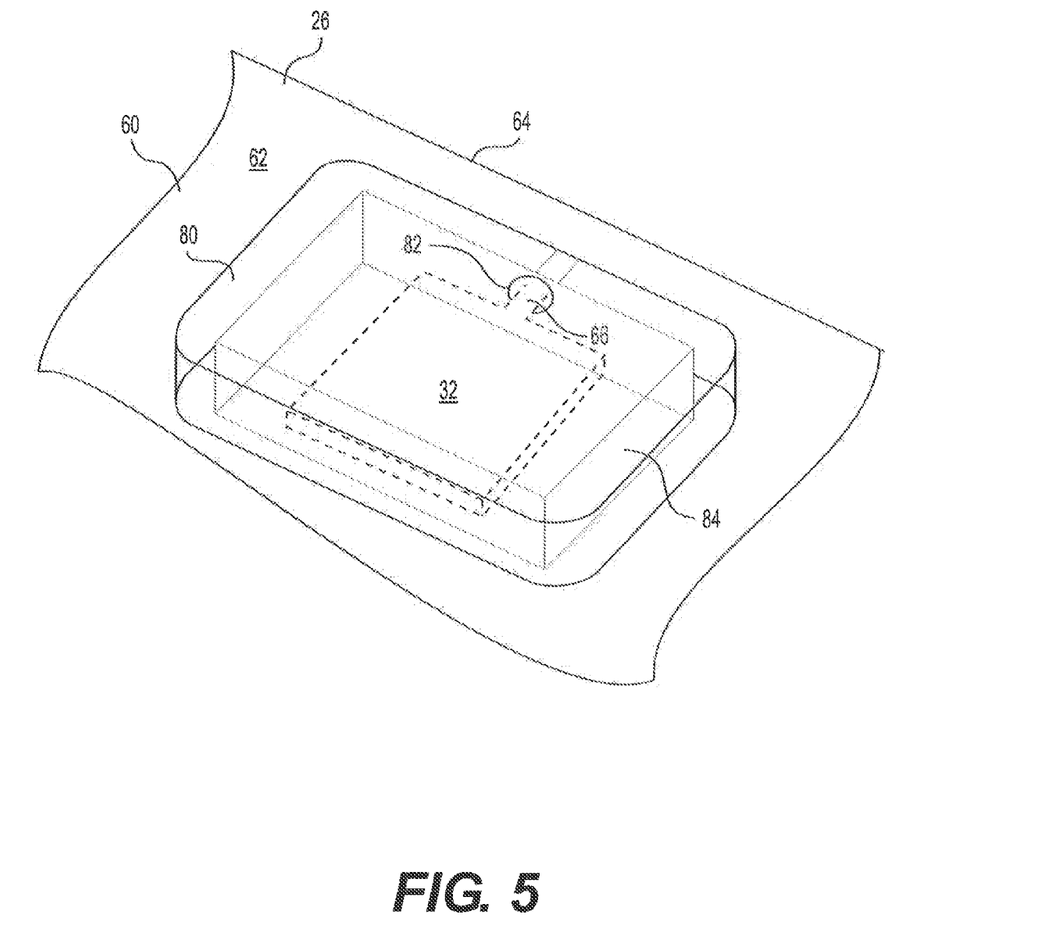
FIG. 5 illustrates an exemplary track link including the sensing device of FIG. 4.

FIG. 5 illustrates an exemplary track link 26 in which a sensing device 32 has been installed. In an exemplary embodiment, track link 26 may include a cavity 80 formed in surface 62. Cavity 80 may be sized and shaped to receive at least a portion of sensing device 32. In some embodiments, a passage 82 may be connected to cavity 80 and configured to receive wear portion 66 of sensing device 32. Passage 82 may extend from cavity 80 to surface 64 such that wear portion 66 may wear away with surface 64.

Sensing device 32 may be positioned in cavity 80 and held in place by a containment mechanism 84. Containment mechanism 84 may be a material, device, or system configured to hold sensing device 32 in place in cavity 80. In one embodiment, containment mechanism 84 may be an encasing material filling cavity 80, with sensing device 32 embedded therein. In another embodiment, containment mechanism 84 may be a housing configured to house sensing device 32 and be received in cavity 80. In some embodiments, containment mechanism 84 may include a cover (not shown) configured to seal an opening into cavity 80 at surface 62. For example, sensing device 32 may be held in place by fasteners (e.g., threaded fasteners) and a cover may close sensing device 32 within cavity 80 to protect sensing device 32 from damage.

While cavity 80 and containment mechanism 84 are depicted and described, it should be understood that there may be other means for mounting sensing device 32 to track link 26. An exemplary process for mounting sensing device 32 to track link 26 and using detection system 54 is described in more detail below.

INDUSTRIAL APPLICABILITY

The exemplary disclosed track link having a wear sensing device may be applicable to a track assembly of any track-type machine. The track link and wear sensing device may be used to monitor a wear parameter associated with the track link and automatically transmit a signal indicative of the wear parameter to a computing device for further use. Since wear of a track link may be indicative of the remaining life of a machine undercarriage (e.g., a chain assembly of the undercarriage), the disclosed embodiments may allow for a determination of a state of a machine undercarriage (e.g., whether critical wear levels have been reached, structural health of the undercarriage, etc.). Further, monitoring of a wear parameter may allow an operator to accurately make inventory part predictions, proactively schedule machine maintenance, and easily and efficiently track wear rates.

In addition, the exemplary disclosed detection system, including an embedded sensing device and strategically positioned communication device, may allow for reliable monitoring of a wear parameter of a track link. Positioning the sensing device within the track link protects the sensing device from damage during use of the associated track assembly and allows the sensing device to be positioned adjacent a wear surface of the track link for accurate detection of a wear parameter (e.g., through corresponding wear of a portion of the sensing device or direct measurement). An exemplary process for mounting sensing device 32 to track link 26 will now be described.

In an exemplary embodiment, an existing (e.g., manufactured) track link 26 may be selected and cavity 80 may be machined therein. In other embodiments, track link 26 may be manufactured (e.g., cast, forged, 3-D printed, etc.) with cavity 80 formed therein. In one embodiment, cavity 80 may be formed as a recess in outward-facing surface 38 of link body 60. In other embodiments, cavity 80 may be located elsewhere on link body 60. Passage 82 may be machined and/or formed adjacent to cavity 80 to receive wear portion 66 of sensing device 32 (in embodiments in which sensing device 32 includes a wear portion 66).

With cavity 80 formed in link body 60, sensing device 32 may be placed in cavity 80 and secured therein by containment mechanism 84. In one embodiment, containment mechanism 84 may be a material configured to fill cavity 80 with sensing device 32 embedded therein. For example, containment mechanism 84 may be a potting epoxy that may be poured/injected into cavity 80 with sensing device 32 positioned therein. The potting epoxy may cure to form a solid material, thereby holding sensing device 32 in place. The material used to embed sensing device 32 may have sufficient strength to prevent damage to sensing device 32 while also being capable of allowing signals to be transmitted therethrough (such that wireless transmissions between sensing device 32 and communication device 34 may be reliably made).

In another embodiment, containment mechanism 84 may be a housing configured to be received in cavity 80. The housing may removably or permanently receive and protect sensing device 32 therein and may be removably or permanently insertable into cavity 80. In one example, the housing may removably receive sensing device 32 therein. In addition, the housing may be removably received in cavity 80 (e.g., the housing may include threads, a detent mechanism, clips, etc., that mate with a corresponding feature of cavity 80). In this way, sensing device 32 (and/or a housing including sensing device 32) may be accessible (e.g., for replacement, service, wired connection, etc.).

As described herein, containment mechanism 84 may be configured to allow signals produced by sensing device 32 to pass therethrough. For example, the material of containment mechanism 84 may be substantially transparent to radio transmissions produced by transceiver 76. Further, when installed on machine 10, track link 26 that includes sensing device 32 may be positioned such that cavity 80 faces away from a center of machine 10. In this way, an exposed portion of containment mechanism 84 may face away from machine 10, thus allowing signals transmitted by sensing device 32 to be more easily broadcast away from track assembly 12 (e.g., and to communication device 34) by avoiding travel solid components of machine 10.

Sensing device 32 mounted to track link 26 may be configured to detect a wear parameter of track link 26. For example, sensing device 32 may include wear portion 66, which may wear away with surface 64 of link body 60 as operation of machine 10 causes such wear. The change in structure of wear portion 66 may allow sensing device 32 to determine a wear parameter of track link 26. For example, when a threshold amount of wear portion 66 is worn away, sensing device 32 may be configured to detect the change and correlate the change with a wear parameter (e.g., a particular amount of material has worn away from surface 64). For instance, controller 72 may detect that a structure of wear portion 66 has changed via circuitry components 70. In another example, sensing device 32 may include a depth sensor configured to measure a dimension of link body 60. Controller 72 may similarly communicate with the depth sensor via circuitry components 70.

Controller 72 may produce a signal indicative of a detected wear parameter. For example, controller 72 may determine that a threshold amount of wear portion 66 has worn away, determine an amount of wear that corresponds to the threshold, and produce a signal indicating the amount of wear. In another embodiment, controller 72 may directly measure the wear parameter (e.g., correlate a current state of wear portion 66 or use a depth sensor to measure a dimension from a set point to surface 64). Transceiver 76 may transmit the signal to communication device 34. Communication device 34 may receive the signal and forward the determined wear parameter to on-board computer 56 and/or off-board computer 58. On-board computer 56 and/or off-board computer 58 may receive the signal and perform one or more processes to inform an operator of the wear parameter, automatically schedule maintenance, update tracked wear information, estimate a remaining life of track link 26 and/or an associated track assembly 12, etc.

Through the exemplary disclosed processes, the disclosed track link 26 and sensing device 32 may provide automatic and/or on-demand monitoring of a wear parameter associated with track link 26. In addition, the use of sensing device 32 in conjunction with on-board computer 56 and/or off-board computer 58 allows wear information to be tracked and analyzed by a computing device and/or an operator (e.g., an operator within machine 10, a supervising operator in a control building, etc.). In this way, track assembly 12 may be monitored and maintained without requiring inefficient manual inspection and without relying on estimates of remaining part life.

It will be apparent to those skilled in the art that various modifications and variations can be made to the track assembly and detection system of the present disclosure without departing from the scope of the disclosure. Other embodiments will be apparent to those skilled in the art from consideration of the specification and practice of the embodiments disclosed herein. It is intended that the specification and examples be considered as exemplary only, with a true scope of the disclosure being indicated by the following claims.

What is claimed is:

1. A track link for a track assembly of a machine, comprising:
    a link body including a wear surface, a cavity formed in the link body in proximity to the wear surface, a passage extending from the cavity to the wear surface, and at least one hole configured to receive a track pin;
    a sensing device positioned in the cavity and configured to generate a signal indicative of a wear parameter of the surface, the sensing device including a wear portion extending through the passage to the wear surface such that as the wear surface wears away, the wear portion also wears away, and the sensing device further including one or more controllers, a memory device, and a transceiver configured to generate the signal and wirelessly broadcast the signal to a communication device on the machine; and
    a containment mechanism configured to secure the sensing device in position inside the cavity.

2. The track link of claim 1, wherein the containment mechanism is a material that fills the cavity with the sensing device embedded therein.

3. The track link of claim 2, wherein the material is a potting epoxy.

4. The track link of claim 1, wherein the containment mechanism is a housing configured to receive the sensing device therein.

5. The track link of claim 4, wherein the sensing device is removably received in the housing.

6. The track link of claim 4, wherein the housing is removably received in the cavity.

7. The track link of claim 1, wherein the sensing device further includes a power source.

8. The track link of claim 7, wherein the power source includes a battery configured to be wirelessly charged.

9. The track link of claim 7, wherein the power source includes a vibration-based energy-harvesting system.

10. A method of installing a sensing device in a track link, comprising:
    forming a cavity in a link body of the track link in proximity to a wear surface of the link body, and forming a passage extending from the cavity to the wear surface;
    positioning the sensing device inside the cavity, the sensing device including a wear portion extending through the passage to the wear surface such that as the wear surface wears away, the wear portion also wears away, and the sensing device further including one or more controllers, a memory device, and a transceiver configured to generate a signal indicative of a wear parameter of the wear surface and wirelessly broadcast the signal to a communication device on the machine; and
    holding the sensing device in position within the cavity with a containment mechanism.

11. The method of claim 10, wherein forming the cavity includes machining the cavity into a second surface.

12. The method of claim 10, wherein holding the sensing device in place within the cavity includes pouring or injecting a potting epoxy into the cavity.

13. The method of claim 10, wherein holding the sensing device in place within the cavity includes positioning the sensing device in a housing and positioning the housing in the cavity.

14. A detection system for a track assembly of a machine, comprising:
    a track link including a wear surface;
    a cavity formed in the track link in proximity to the wear surface, a passage extending from the cavity to the wear surface;
    a sensing device secured to the track link within the cavity and configured to detect a wear parameter of the wear surface, the sensing device including a wear portion extending through the passage to the wear surface such that as the wear surface wears away, the wear portion also wears away, and the sensing device further including one or more controllers, a memory device, and a transceiver configured to generate a signal indicative of the wear parameter of the wear surface and wirelessly broadcast the signal to a communication device mounted to the machine; and
    wherein the communication device is configured to transmit a corresponding signal indicative of the wear parameter to a computing device.

15. The detection system of claim 14, wherein the track link includes a containment mechanism configured to:
    secure the sensing device inside the cavity, and
    allow the signal to pass therethrough,
    wherein an exposed portion of the containment mechanism faces away from the machine.

* * * * *